(12) United States Patent
Kojiro et al.

(10) Patent No.: US 7,115,568 B2
(45) Date of Patent: Oct. 3, 2006

(54) METHODS USING TCF II

(75) Inventors: Masamichi Kojiro, Fukuoka (JP); Hirohisa Yano, Fukuoka (JP); Akihiro Iemura, Fukuoka (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 284 days.

(21) Appl. No.: 10/267,906

(22) Filed: Oct. 9, 2002

(65) Prior Publication Data

US 2003/0082134 A1 May 1, 2003

Related U.S. Application Data

(63) Continuation of application No. 09/180,586, filed on Jul. 29, 1999, now abandoned.

(51) Int. Cl.
*A61K 38/16* (2006.01)

(52) U.S. Cl. .......................... 514/12; 530/350

(58) Field of Classification Search .................... 514/2, 514/12
See application file for complete search history.

(56) References Cited

U.S. PATENT DOCUMENTS

| | | | |
|---|---|---|---|
| 3,904,753 A | 9/1975 | Sonenberg et al. | 424/177 |
| 4,076,701 A | 2/1978 | Burton et al. | |
| 4,481,137 A | 11/1984 | Ohnishi et al. | 260/112 |
| 4,490,549 A | 12/1984 | Johnson | |
| 4,650,674 A | 3/1987 | Aggarwal et al. | |
| 4,777,241 A | 10/1988 | Irikura et al. | |
| 4,822,605 A | 4/1989 | Powell | |
| 4,870,163 A | 9/1989 | Rubin et al. | |
| 5,091,511 A | 2/1992 | Sone et al. | |
| 5,328,836 A | 7/1994 | Shima et al. | 435/69.4 |
| 5,362,716 A | 11/1994 | Kmiecik et al. | 514/12 |
| 5,432,267 A | 7/1995 | Kusama et al. | 536/17.9 |
| 5,510,327 A | 4/1996 | Hayasaka et al. | 514/8 |
| 5,547,856 A | 8/1996 | Godowski et al. | 435/694 |
| 5,587,359 A | 12/1996 | Higashio et al. | 514/12 |
| 5,589,451 A | 12/1996 | Wilson | 512/2 |
| 5,606,029 A | 2/1997 | Degen | 530/399 |
| 5,648,233 A | 7/1997 | Yamaguchi et al. | 435/69.1 |
| 5,648,273 A | 7/1997 | Bottaro et al. | 435/501 |
| 5,658,742 A | 8/1997 | Higashio et al. | 435/7.9 |
| 5,703,047 A | 12/1997 | Wilson | 514/12 |
| 5,703,048 A | 12/1997 | Roos et al. | 514/12 |
| 5,707,624 A | 1/1998 | Nickoloff et al. | 424/158.1 |
| 5,714,461 A | 2/1998 | Masunaga et al. | 514/8 |
| 5,760,177 A | 6/1998 | Iwanaga et al. | 530/350 |
| 5,776,464 A | 7/1998 | Nakamura | 424/198.1 |
| 5,821,223 A | 10/1998 | Rubin et al. | 514/12 |
| 5,998,370 A | 12/1999 | Arai | 514/12 |
| 6,306,827 B1 | 10/2001 | Kinosaki et al. | |
| 6,333,309 B1 * | 12/2001 | Higashio et al. | 514/12 |

FOREIGN PATENT DOCUMENTS

| | | |
|---|---|---|
| CA | 2218864 | 10/1997 |
| CA | 2100720 C | 3/2003 |
| CA | 2116192 C | 5/2005 |
| EP | 0 322 084 | 6/1989 |
| EP | 0 456 188 A1 | 11/1991 |
| EP | 0 498 680 A1 | 8/1992 |
| EP | 0 519 728 A2 | 12/1992 |
| EP | 0 587 311 A1 | 3/1994 |
| EP | 0 588 477 A2 | 3/1994 |
| EP | 0 604 184 A1 | 6/1994 |
| EP | 0 604 185 A1 | 6/1994 |
| EP | 0 462 277 B1 | 6/1995 |
| EP | 0 672 685 A2 | 9/1995 |
| EP | 0 724 884 A1 | 7/1996 |
| EP | 0 462 549 B1 | 8/1996 |
| EP | 0 757 994 A1 | 2/1997 |
| EP | 0 821 969 A2 | 2/1998 |
| EP | 0 461 560 B1 | 11/1998 |
| EP | 0 891 778 A2 | 1/1999 |
| EP | 0 539 590 B1 | 3/1999 |
| EP | 0 914 829 A1 | 5/1999 |
| EP | 0 925 791 A1 | 6/1999 |
| EP | 0 950 416 A1 | 10/1999 |
| EP | 0 982 037 A1 | 1/2000 |
| EP | 0 612 530 B1 | 8/2000 |
| EP | 0 653 211 B1 | 10/2001 |
| JP | 10-68400 | 3/1989 |
| JP | 5-244976 | 9/1993 |
| JP | 6-40935 | 2/1994 |
| JP | 6-40938 | 2/1994 |
| JP | 06040934 | 2/1994 |
| JP | 6-56692 | 3/1994 |
| JP | 6-116299 | 4/1994 |
| JP | 06340546 | 12/1994 |
| JP | 081176007 | 7/1996 |

(Continued)

OTHER PUBLICATIONS

Anscher et al., "Role of Transforming Growth Factor-.beta. and Hepatocyte Growth Factor in Late Normal Tissue Effects of Radiation," *Radiat. Oncol. Invest.* 1 (6), 305-13 (1994).

(Continued)

*Primary Examiner*—Michael Borin
(74) *Attorney, Agent, or Firm*—Kirkpatrick & Lockhart Nicholson Graham LLP

(57) ABSTRACT

The present invention provides an agent for preventing and/or treating cachexia comprising TCF-II as an effective ingredient. An agent for preventing and treating cachexia caused by cancer, acquired immunodeficient syndrome (AIDS), cardiac diseases, infectious disease, shock, burn, endotoxinemia, organ inflammation, surgery, diabetes, collagen diseases, radiotherapy, chemotherapy is provided by the present invention.

4 Claims, 2 Drawing Sheets

FOREIGN PATENT DOCUMENTS

| JP | 08231418 | 9/1996 |
|---|---|---|
| JP | 10-29951 | 2/1998 |
| JP | 10-194986 | 7/1998 |
| JP | 10-273446 | 10/1998 |
| WO | WO90/10651 | 9/1990 |
| WO | WO91/03254 | 3/1991 |
| WO | WO93/08821 | 5/1993 |
| WO | WO93/13066 | 7/1993 |
| WO | WO94/14845 | 7/1994 |
| WO | WO96/20004 | 7/1996 |
| WO | WO96/20214 | 7/1996 |
| WO | WO96/28423 | 9/1996 |
| WO | WO96/32960 | 10/1996 |
| WO | WO98/40096 | 9/1998 |
| WO | WO98/41230 | 9/1998 |
| WO | WO98/43665 | 10/1998 |
| WO | WO99/47155 | 9/1999 |

OTHER PUBLICATIONS

Argiles et al, "The Role of Cytokines in Cancer Cachexia," Department di Bioquimica i Biologia Molecular, Facultat de Biologia, Universitat de Barcelona, Spain; Med Res Rev. vol. 19 (3):223-48 (May 1999).

Bervetello et al., "Heterogeneous Response of Adipose Tissue to Cancer Cachexia," *Braz. J. Med. Biol. Res.*, vol. 34(9), pp. 1161-1167 (2001).

Bossola et al., "Serum Tumour Necrosis Factor-α Levels in Cancer Patients are Discontinuous and Correlate with Weight Loss," *European Journal of Clinical Investigation*, vol. 30, pp. 1107-1112 (2000).

Ceconi, et al., "Tumor Necrosis Factor in Congestive Heart Failure: A Mechanism of Disease for the New Millennium?" *Progress in Cardiovascular Diseases*, vol. 41, No. 1, Suppl. 1, pp. 25-30, (Jul./Aug. 1998).

Chang, et al., "The Role of Cytokines in the Catabloc Consequences of Infection and Injury, Journal of Parental and Enteral Nutrition," vol. 22, No. 3, 156-166 (May/Jun. 1998).

Fujiwara et al., "Stimulation of Liver Growth by Exogenous Human Hepatocyte Growth Factor in Normal and Partially Hepatectomized Rats," *Hepatology*, 18(6):1443-1449 (1993).

Gohda et al., "Purification and Partial Characterization of Hepatocyte Growth Factor from Plasma of a Patient with Fulminant Hepatic Failure," *The American Society for Clinical Investigation*, vol. 81, pp. 414-419 (Feb. 1988).

Raymond C. Harris, "Growth Factors and Cytokines in Acute Renal Failure," *Supplement to Advances in Renal Replacement Therapy*, vol. 4, No. 2, Suppl. 1, pp. 43-53 (Apr. 1997).

Haslett, "Anticytokine Approaches to the Treatment of Anorexia and Cachexia, Seminars in Oncology," vol. 25, No. 2 Suppl. 6, pp. 53-57, (Apr. 1998).

Higashio et al., "Identity of a Tumor Cytotoxic Factor From Human Fibroblasts and Hepatocyte Growth Factor," *Biochemical and Biophysical Research Communications*, 170(1):397-404, (Jul. 16, 1990).

Higashio et al., "Tumor cytotoxic activity of HGF-SF," *Experientia Supplementum*, 65:351-368 (1993).

Humes et al., "Renal Tubule Cell Repair following Acute Renal Injury," *Mineral and Electrolyte Metabolism*, vol. 21, pp. 353-365, (Jul./Oct. 1995).

Kinosaki et al., "Identification of heparin-binding stretches of a naturally occurring deleted variant of hepatocyte growth factor (dHGF)," *Biochimica et Biophysica Acta*, 1384(1): 93-102 (1998).

Kinosaki et al., "Analysis of deleted variant of hepatocyte growth factor by alanine scanning mutagenesis: identification of residues essential for its biological function and generation of mutants with enhanced mitogenic activity on rat hepatocytes," *FEBS Letters*, 434(1-2):165-169 (1998).

Llovera, et al., "Protein Turnover in Skeletal Muscle of Tumor-Bearing Transgenic Mice Overexpressing the Soluble TNF Receptor-1," *Cancer Letters*, 130, 19-27 (1998).

Llovera, et al., "Role of TNF Receptor 1 in Protein Turnover During Cancer Cachexia Using Gene Knockout Mice," *Molecular and Cellular Endocrinology*, 142, 183-189 (1998).

Masunaga et al., "Amelioration of Disordered Hepatic Protein Synthesis by the Deleted Form of Hepatocyte Growth Factor in Models of Liver Failure in Rats," *Journal of Pharmacy and Pharmacology*, 48:876-879 (1996).

Masunaga et al., "Deleted form of hepatocyte growth factor (dHGF) increases the number of platelets in rats with liver cirrhosis," *Liver*, 17(4):192-197 (1997).

Masunaga et al., "Preventive effects of the deleted form of hepatocyte growth factor against various liver injuries," *European Journal of Pharmacology*, vol. 342, pp. 267-279 (1998).

Matsuda et al., "Hepatocyte Growth Factor Suppresses the Onset of Liver Cirrhosis and Abrogates Lethal Hepatic Dysfunction in Rats," *J. Biochem*, vol. 118, No. 3, pp. 643-649 (1995).

Matsumoto et al., "HGF: its organotrophic role and therapeutic potential," Therapeutic Potential of HGF, Ciba Foundation Symposium 212:198-214; discussion 211-4 (1997).

Matsumoto et al., "Roles of HGF as a pleiotropic factor in organ regeneration," *Hepatocyte Growth Factor-Scatter Factor*, (1993).

Miyazawa et al., "Molecular Cloning and Sequence Analysis of cDNA for Human Hepatocyte Growth Factor," 164(2):967-973 (Sep. 15, 1989).

Morimoto et al., "Hepatocyte Growth Factor Modulates Migration and Proliferation of Human Microvascular Endothelial Cells in Culture," *Biochemical and Biophysical Research Communications*, 179(2):1042-1049 (Sep. 16, 1991).

Nagoshi et al., "Hepatocyte apoptosis and hepatic expression of transforming growth factor-β mRNA during involution of hyperplastic rat liver induced by hepatocyte growth factor," *Journal of Gastroenterology and Hepatology*, 13(8):786-793 (1998).

Nishimura, et al., "Serum Hepatocyte Growth Factor as a Possible Indicator of Arteriosclerosis," *Journal of Hypertension*, 15:1137-1142 (1997).

Ronenn Roubenoff, "The Pathophysiology of Wasting in the Elderly," Clinical Trials for the Treatment of Secondary Wasting and Cachexia, American Society for Nutritional Sciences, pp. 256S-259S (1999).

Rubin et al., "A Broad-Spectrum Human Lung Fibroblast-Derived Mitogen is a Variant of Hepatocyte Growth Factor," *Proc. Natl. Acad. Sci. USA*, 88: 415-419 (1991).

Francesco Paolo Schena, "Role of growth factors in acute renal failure," *Kidney International*, vol. 53, Suppl. 66, pp. S-11-S-15 (1998).

Seki et al., "Isolation and Expression of cDNA for Different Forms of Hepatocyte Growth Factor From Human Leukocyte," *Biochemical and Biophysical Research Communications*, 172(1): 321-327 (1990).

Shima et al., "Possible Involvement of p21/wafl in the Growth Inhibition of HepG2 Cells Induced by Hepatocyte Growth Factor," *Journal of Cellular Physiology*, 177(1):130-136 (1998).

Shima et al., "Hepatocyte Growth Factor and its Variant with a Deletion of Five Amino Acids are Distinguishable in their Biological Activity and Tertiary Structure," *Biochemical and Biophysical Research Communications*, 200(2):808-815 (Apr. 29, 1994).

Shima et al., "Tumor Cytotoxic Factor/Hepatocyte Growth Factor from Human Fibroblasts: Cloning of its cDNA, Purification and Characterization of Recombinant Protein," *Biochemical and Biophysical Research Communications*, 180(2):1151-1158 (Oct. 31, 1991).

Shima et al., "ELISA for F-TCF (human hepatocyte growth factor/hHGF)/fibroblast-derived tumor cytotoxic factor antigen employing monoclonal antibodies and its application to patients with liver diseases," *Gastroenterologia Japonica*, 26(4):477-482 (1991).

Shima et al., "A Fibroblast-Derived Tumor Cytotoxic Factor/F-TCF (Hepatocyte Growth Factor/HGF) Has Multiple Functions in Vitro," *Cell Biology International Reports*, 15(5):397-407 (1991).

Shima et al., "Structure and Biological Property of Fibroblast-Derived Tumor Cytotoxic Factor (F-TCF)," *Nippon Rinsho*, vol. 50, No. 8, pp. 1962-1966 (1992).

Shiota et al., "Hepatocyte Growth Factor Inhibits Growth of Hepatocellular Carcinoma Cells," *Proc. Natl. Acad. Sci. USA*, vol. 89, pp. 373-377 (Jan. 1992).

Tajima et al., "Hepatocyte Growth Factor has Potent Anti-Proliferative Activity in Various Tumor Cell Lines", *Federation of European Biochemical Societies*, 291(2):229-232 (Oct. 1991).

Takehara et al., "Structure and Function of Hepatocyte Growth Factor," *Tanpakushitsu Kakusan Koso*, vol. 36, No. 7, pp. 1227-1236 (1991).

Tamura et al., "Enhancement of Human Hepatocyte Growth Factor Production by Interleukin-1α and -1β and Tumor Necrosis Factor-α by Fibroblasts in Culture," *J. Biol. Chem.*, 268(11), 8140-5 (1993).

Michael J. Tisdale, "Biology of Cachexia," *Journal of the National Cancer Institute*, vol. 89, No. 23 (Dec. 3, 1997).

Tracey et al., "Cachectin/Tumor Necrosis Factor Induces Cachexia, Anemia, and Inflammation," Laboratory of Surgical Metabolism, New York Hospital-Cornell University Medical Center, New York, NY 10021; *J Exp Med*, vol. 167(3):1211-27 (Mar. 1988).

Uematsu et al., "Effective Administration Route for the Deleted Form of Hepatocyte Growth Factor to Exert its Pharmacological Effects," *Journal of Pharmaceutical Sciences*, 88(1):131-135 (Jan. 1999).

Weidner et al., "Evidence for the Identity of Human Scatter Factor and Human Hepatocyte Growth Factor," *Proc. Natl. Acad. Sci. USA*, vol. 88, pp. 7001-7005 (Aug. 1991).

Yamaguchi et al., "Recombinant Human Hepatocyte Growth Factor Facilitates Biliary Transport After Hepatocyte Transplantation in Eisai Hyperbilirubinemic Rats," *Digestive Diseases and Sciences*, 42(3):522-528 (Mar. 1997).

Yamashita et al., "Effects of the Deleted Form of Hepatocyte Growth Factor on Serum Hyaluronate Levels in Rats with Liver Cirrhosis," *Journal of Veterinary Medical Science*, 60(3):359-360 (1998).

Yang, et al., "Effects of Vascular Endothelial Growth Factor on Hemodynamics and Cardiac Performance," *Journal of Cardiovascular Pharmacology*, 27: 838-844 (1996).

Yano et al., "Natural hepatocyte growth factor (HGF) from human serum and a bound form of recombinant HGF with heparan sulfate are indistinguishable in their physiochemical properties," *International Journal of Biological Macromolecules*, 23(3):227-235 (1998).

Yasuda et al., "Antifibrogenic Effect of a Deletion Variant of Hepatocyte Growth Factor on Liver Fibrosis in Rats," *Hepatology*, 24(3):636-642 (1996).

Merryman et al., "Effects of Gallium Nitrate in Nude Mice Bearing a Canine Adenocarcinoma (CAC-8) Model of Humoral Hypercalcemia of Malignancy," *J.Bone Miner Res.* 9(5), 725-32, 1994.

Zembala et al., "The MHC Class-II and CD44 Molecules Are Involved In The Induction of Tumour Necrosis Factor (TNF) Gene Expression By Human Monocytes Stimulated With Tumour Cells," *Int.J.Cancer* 56(2), 269-74, 1994.

Zhou et al., "Role of NF-κB and Cytokine in Experimental Cancer Cachexia," *World J. Gastroenterol* 9(7), 1567-1570, 2003.

Li et al., "Mechanism and Treatment of Cancer Cachexia in Tumor-Bearing Mice," *Chin J. Oncoli* 19(3): 188-91, May 1997 (Abstract in English).

Ashorn, et al., (1990), "An Inhibitor of the Protease Blocks Maturation of Human and Simian Immunodeficiency Viruses and Spread of Infection," *Proc. Natl. Acad. Sci.*, 87:7472-7476.

Baldwin, et al., (1995), "Structure of HIV-1 Protease with KNI-272, A Tight-Binding Transition-State Analog Containing Allophenylnorstatine," *Structure*, 3(6):81-588.

Bone, (1991), "The Pathogenesis of Sepsis," *Annals of Internal Medicine*, 115(6):457-469.

Cerra et al., (1987), "Hypermetabolism, organ failure, and metabolic support," *Surgery*, vol. 101, 1-14.

Cross et al., (1993), "Choice of Bacteria in Animal Models of Sepsis," *Infection and Immunity*, 61:2741-2747.

Debouck, et al., (1990), "Human Immunodeficiency Virus Protease: A Target for AIDS Therapy," Drug Development Research, 21:1-17.

Deitch, (1992), "Multiple Organ Failure," *Annals of Surgery*, 216(2):117-134.

Deitch et al., (1999), "Prevention of Multiple Organ Failure," *Surgical Clinics of North America*, 79(6):1471-1488.

Dube et al., (1988), "Glycosylation at Specific Sites of Erythropoietin Is Essential for Biosynthesis, Secretion, and Biological Function," *Journal of Biological Chemistry*, 263(33):17516-17521.

Fahey et al., (1992), "Status of Immune-Based Therapies In HIV Infection and AIDS" *Clin.. Exp. Immunol.*, 88:1-5.

Fink et al., (1990), "Laboratory Models of Sepsis and Shock," *Journal of Surgical Research*, 49:186-196.

Glauser et al., (1991), "Septic Shock: Pathogenesis," *The Lancet*, 338:732-736.

Goodman & Gilman, *The Pharmacological Basis of Therapeutics*, 9th Edition, pp. 1654-1659.

Goto, M. et al., "Production of Recombinant Human Erythropoietin in mammalian Cells: Host-Cell Dependency of the Biological Activity of the Cloned Glycoprotein." *Bio/Technology*, vol. 6, pp. 67-71 (Jan. 1988).

Gross et al., (1993), "Inflammatory Mediators and Cytokines—New Aspects of the Pathophysiology and Assessment of Severity of Acute Pancreatitis?," *Hepato-Gastroenterol.*, 40:522-530.

Gulnik, et al., (1995), "Kinetic Characterization and Cross-Resistance Patterns of HIV-1 Protease Mutants A Selected under Drug Pressure," *Biochemistry*, 34:9282-9287.

Haynes et al., (1996), "Update on the Issues of HIV Vaccine Development," *Annals of Medicine*, 28:39-41.

Hernandez, et al., (1992), "Characterization of the Effects of Human Placental HGF on Rat Hepatocytes," *Journal of Cellular Physiology*, 150:116-121.

Hoffman et al., (1992), "Scatter Factor is a Glycoprotein but Glycosylation is not Required for its Activity", *Biochimica et Biophysica Acta*, 1120:343-350.

Holzheimer et al., (1997), "The Challenge of Postoperative Infections: Does the Surgeon Make a Difference," *Infection Control and Hospital Epidemiology*, 18(6):449-456.

Holzheimer, (2001), "Antibiotic Induced Endotoxin Release and Clinical Sepsis: a Review," *Journal of Chemotherapy*, 13 (1):159-172.

Horton et al., (1987), "Hemodynamic Function in Acute Pancreatitis," *Surgery*, 103:538-546.

Hughes et al., (1996), "Inhibition of TNFa Improves Survival in an Experimental Model of Acute Pancreatitis," *American Surgeon*, 62:8-13.

Humphrey et al., (1997), "Removal of Human Immunodeficiency Virus Type 1 (HIV-1) Protease Inhibitors from Preparations of Immature HIV-1 Virions Does Not Result in an Increase in Infectivity or the Appearance of Mature Morphology," *Antimicrobial Agents and Chemotherapy,*:1017-1023.

Humphrey et al., (1996), "A Phase I Trial of HIV Protease Inhibitor KNI-272 in Patients with AIDS or Symptomatic HIV Infection," *Int. Conf. AIDS* Jul. 7-12, 1996, 11:77 (abstract No. Mo.B.1132).

Jiji Press, "Anti-AIDS Drug Tests Go to Britain," *Japan Times*, (1995).

Kageyama et al., (1993), "In Vitro Anti-Human Immunodeficiency Virus (HIV) Activities of Transition State Mimetic HIV Protease Inhibitors Containing Allophenylnorstatine," *Antimicrobial Agents and Chemotherapy,*: 810-817.

Kageyama et al., (1992), "In Vitro Inhibition of Human Immunodeficiency Virus (HIV) Type 1 Replication by C2 Symmetry-Based HIV Protease Inhibitors as Single Agents or in Combinations," *Antimicrobial Agents and Chemotherapy,*:926-933.

Kaneshima et al., (1991), "Human Immunodeficiency Virus Infection of Human Lymph Nodes in the SCID-hu Mouse," *Proc. Natl. Acad. Sci.*, 88:4523-4527.

Karzai et al., (1997), "Immune Modulation and Sepsis," *Int. J. Clin. Pract.*, 51(4):232-237.

Kien et al., (1996), "Small-Volume Resuscitation Using Hypertonic Saline Improves Organ Perfusion in Burned Rats," *Anesth. Analg.*, 83:782-788.

Kiso, (1995), "Design and Synthesis of HIV Protease Inhibitors Containing Allophenylnorstatine As A Transition-State Mimic," *Adv. Exp. Med. Biol.,*: 362:413-423.

Kondo et al., (1999), "Effects of Deletion-Type Human Hepatocyte Growth Factor on Murine Septic Model," *Journal of Surgical Research*, 85:88-95.

Kozlel et al., "HLA Class I—Restricted Cytotoxic T Lymphocytes Specific for Hepatitis C Virus," *J. Clin. Invest.*, vol. 96, Nov. 1995, 2311-2321.

Lehtola et al., (1986), "Effects of Dextran 70 Versus Crystalloids in the Microcirculation of Porcine Hemorrhagic Pancreatitis," *Surgery, Gynecology & Obstetrics*, 162:556-562.

Lungarella et al., (1985), "Pulmonary Vascular Injury in Pancreatitis: Evidence for a Major Role Played by Pancreatic Elastase," *Experimental and Molecular Pathology*, 42:44-59.

Mastrangelo et al., (2000), "Sepsis Decreases the Spontaneous and Agonist-Induced Contractile Activities in the Rat Portal Vein," *Journal of Hepatology*, 33:933-940.

Meek, (1992), "Inhibitors of HIV-1 Protease," *J. Enzyme Inhibition*, 6:65-98.

Meek et al., (1990), "Inhibition of HIV-1 Protease in Infected T-Lymphocytes by Synthetic Peptide Analogues," *Nature*, 343:90-92.

Merryman et al., (1994), "Effects of Gallium Nitrate in Nude Mice Bearing a Canine Adenocarcinoma (CAC-8) Model of Humoral Hypercalcemia of Malignancy," *J.Bone Miner. Res.*, 9(5):725-32.

McCune et al., (1990), "Suppression of HIV Infection in AXT-Treated SCID-hu Mice," *Science*, 247:564-565.

Mimoto et al., (1991), "Rational Design and Synthesis of a Novel Class of Active Site-Targeted HIV Protease Inhibitors Containing a Hydroxymethylcarbonyl Isostere. Use of Phenylnorstatine or Allopheylnorstatine as a Transition-State Mimic," *Chem. Pharm. Bull.*, 39(9):2465-2467.

Mimoto et al., (1992), "Kynostatin (KNI)-227 and -272, Highly Potent Anti-HIV Agents: Conformationally Constrained Tripeptide Inhibitors of HIV Protease Containing Allophenylnorstatine," *Chem. Pharm. Bull.*, 40(8):2251-2253.

Moody (1982), "Changes in the serum concentrations of thyroxine-binding prealbumin and retinol-binding protein following burn injury," *Clinica Chimica Acta*, 118:87-92.

Moody et al., (1985), "The effects of septic complications upon the serum protein changes associated with thermal injury," *Ann. Clin. Biochem.*, 22:391-396.

Ohlsson et al., (1991), "Pathophysiology of Acute Pancreatitis," Chapter 20 in *Pancreatic Disease, Progress and Prospects*, Journal et al., (eds.) pp. 213-226, New York: Springer-Verlag.

Ohnishi et al., (1984), "Effects of Urinary Trypsin Inhibitor on Pancreatic Enzymes and Experimental Acute Pancreatitis," *Digestive Diseases and Sciences*, 29(1):26-32.

Penner, (1998), "Disseminated Intravascular Coagulation in Patients with Multiple Organ Failure of Non-Septic Origin," *Seminars in Thrombosis and Hemostatis*, 24(1):45-52.

Renner et al., (1985), "Death Due to Acute Pancreatitis: A Retrospective Analysis of 405 Autopsy Cases," *Digestive Diseases and Sciences*, 30(10): 1005-1018.

Roberts et al., (1990), "Rational Design of Peptide-Based HIV Proteinase Inhibitors," *Science*, 248:357-361.

Robins et al., (1993), "HIV Protease Inhibitors: Their Anti-HIV Activity and Potential Role in Treatment," *Journal of Acquired Immune Deficiency Syndromes*, 6:162-170.

Romero et al., (1991), "Nonnucleoside Reverse Transcriptase Inhibitors That Potently and Specifically Block Human Immunodeficiency Virus Type 1 Replication," *Proc. Natl. Acad. Sci.*, 88:8806-8810.

Sayek et al., (1997), "Septic Complications after Biliary Tract Stone Surgery: A Review and Report of the European Prospective Study," *Hepato-Gastroenterology*, 44:959-967.

Schmaier, (2004), "Disseminated Intravascular Coagulation," accessed online at http://www.emedicine.com/MED/topic577.htm on Sep. 10, 2004.

Shih, et al., (1991), "Postexposure Prophylaxis with Zidovudine Suppresses Human Immunodeficiency Virus Type 1 Infection in SCID-hu Mice in a Time-Dependent Manner," *The Journal of Infectious Diseases*, 163:625-627.

Sone, (1989), "Effector Mechanism of Human Monocyte-Mediated Cytotoxicity: Role of a New Tumor Cytotoxic Factor Distinct from Interleukin 1 and Tumor Necrosis Factor .alpha.," *Biotherapy*, 1:233-243.

Sone, (1985), "Kinetics and Function of Tumor Cytotoxic Factor(s) Produced by Human Blood Monocytes Activated to the Tumoricidal State," *JNCI*, 74(3):583-590.

Sone, (1986), "Potentiation of Direct Antitumor Cytotoxicity and Production of Tumor Cytolytic Factors in Human Blood Monocytes by Human Recombinant Interferon-Gamma and Muramyl Dipeptide Derivatives," *Cancer Immunol. Immunother.*, 21:93-99.

Streat, (1987), "Nutritional Support in the Management of Critically Ill Patients in Surgical Intensive Care," *World J. Surg.*, 11(2):194-201.

Tahamont et al., (1982), "Increased Lung Vascular Permeability After Pancreatitis and Trypsin Infusion," *American Journal of Pathologists*, 109:15-26.

Tam et al., (1992), "Intriguing Structure-Activity Relations Underlie the Potent Inhibition of HIV Protease by Norstatine-Based Peptides," *Journal of Medicinal Chemistry*, 35(7):1317-1320.

Tanaka et al., (1995), "Interleukin-1 receptor antagonist modifies the changes in vital organs induced by acute necrotizing pancreatitis in a rat experimental model," *Critical Care Medicine*, 23(5):901-908.

Uchida et al., (1997), "HIV-1 Protease Does Not Play A Critical Role in the Early Stages of HIV-1 Infection," *Antiviral Research*, 36:107-113.

Ueda et al., (1996), "Significant Elevation of Serum Human Hepatocyte Growth Factor Levels in Patients with Acute Pancreatitis," *Pancreas*, 12(1):76-83.

Wichterman et al., (1980), "Sepsis and Septic Shock: A Review of Laboratory Models and a Proposal," *Journal of Surgical Research*, 29: 189-201.

Wilson et al., (1998), "Acute Pancreatitis as a model of Sepsis," *Journal of Antimicrobial Chemotherapy*, 41(Suppl. A):51-63.

Windsor et al., (1988), "Weight Loss with Physiologic Impairment: A Basic Indicator of Surgical Risk," *Ann. Surg.*, 207(3):290-296.

Xia et al., (1992), "The Effects of Burn Injury on the Acute Phase Response," *Journal of Trauma*, 32(2):245-251.

Xu et al., (1998), "Prolonged Immunodepression After Trauma and Hemorrhagic Shock," *Journal of Trauma Injury, Infection and Critical Care*, vol. 44(2), 335-341.

Yajima, et al., (1989), "Non-Septic Endotoxemia in Cirrhotic Patients," *Gastroenterologia Japonica*, 24(3):262-269.

Yamaguchi et al., (1991), "Effects of Site-directed Removal of N-Glycosylation Sites in Human Erythropoietin on Its Production and Biological Properties," *The Journal of Biological Chemistry*, 266(30):20434-20439.

Zeng, et al., (1996), "Prevention of Endotoxic Shock in Rats with Hepatic Stimulating Substance," *Chinese Journal of Internal Medicine*, 35:99-102 (Abstract only).

Zipp, et al., (1995), "Physical Chemical Characterization of the HIV-Protease Inhibitor Clinical Candidate," *Abstracts of the 35th ICAAC*, (1995).

Gore et al., (1999), "Review of Colloids as Fluid Resuscitation for Burn Patients," *Jpn. J. Burn Inj.*, 25(2):11-17.

Takehara et al., (1991), "The Structure of Hepatocyte Growth Factor (HGF) and its Physiological Activity," *Tanpakushitsu Kakusankoso*, 36(7):1227-1236 (abstract only).

Tamakuma et al., (1989), "Cancerous cachexia and Cachectin," *Strides of Medicine*, 149(5):371:373 (abstract only).

\* cited by examiner

METHODS USING TCF II

SUMMARY OF THE INVENTION

The present invention relates to an agent for preventing and/or treating cachexia comprising Tumor Cytotoxic Factor-II (TCF-II) or hepatocyte growth factor (HGF) as an effective ingredient. In particular, the present invention relates to the use of TCF-II or HGF as agent for preventing and treating cachexia caused by one of the factors selected from the group consisting of cancer, acquired immunodeficient syndrome (AIDS), cardiac diseases, infectious disease, shock, burn, endotoxinemia, organ inflammation, surgery, diabetes, collagen diseases, radiotherapy, chemotherapy is provided by the present invention.

BACKGROUND OF THE INVENTION

Generally, a disease such as cancer, acquired immunodeficiency (AIDS), cardiac disease will accompany with anorexia, weight loss, physical exhaustion, marasmus, dermatrophia, xerosis, anemia, edema, abnormal blood coagulation-fibrinolysis and this pathology is defined as cachexia. After suffering from this systemic marasmus, a patient will eventually die (Tamaguma, M. et. al., Igakunoayumi, 149, 371–373 (1989)). Further, if radiotherapy and/or chemotherapy is carried out for a patient with progressive or terminal cancer for whom curative operation can not be expected, it may lead to extremely lowered biological body defensive function such as immunological function due to specific malnutrition, resulting in shortening life. Therefore, there are serious problems in practical treatment of cachexia. The cause of cachexia has been so far considered to be triggered by imbalance of nutritional equilibrium resulting from lowered nutrition intake combined with increased nutrition consumption, along with affection of humoric factors mobilized from the cancer or tile lesion oil systemic metabolism. In the above situations, positive alimentation is carried out using total parental nutrition in order to supplement extreme nutritional or energetic deficiency and enhance immunological function in the treatment of cachexia. However, in cachexia, intake of energy will be used not for saving patient's life but for proliferation of tumor cells, so that alimentation can not be sufficient for a cachexic patient.

Recently, monokines or cytokines, such as Tumor Necrosis Factor (TNF) mobilized from macrophage, have been implicated in the pathogenesis of cachexia. TNF was found as a factor of affecting tumor cells and elucidated to be secreted by macrophages which is one of immunocytes and has a phagocytic action. Though it was originally studied as a potential anti-cancer drug because of its direct cytotoxic effect and strong anti-tumor activity, recently various kinds of action of TNF have been investigated since it was found that TNF may cause cachexia that is marasmus including weight loss of a patient with cancer, severe infectious disease, or a ringleader cytokine induced inflammation. The main actions of TNF are: (1) osteoclastic action, (2) induction of hyperlipidemia by inhibition of uptake of lipid into cell, (3) induction of production of interleukin 1 and colony stimulation factor, (4) impairment of angioendotherial cell, and (5) intervening reaction of exotoxin shock in grave infectious disease.

Though an agent for treating cachexia accompanied with cancer, acquired immunodeficient syndrome (AIDS), cardiac diseases, infectious disease, shock, burn, endotoxinemia, organ inflammation, or these diseases themselves or various kinds of inflammatory diseases including chronic rheumatoid arthritis and inflammatory gut disease are expected to be developed, in fact, there is no satisfactory agent available at present.

The present inventors found that TCF-II known as tumor cytotoxic factor has an excellent effect of preventing and treating cachexia. Accordingly, the present invention relates to an agent for preventing and/or treating cachexia comprising TCF-II as an effective ingredient.

An agent for preventing and treating cachexia caused by one of the factors selected from the group consisting of cancer, acquired immunodeficient syndrome (AIDS), cardiac diseases, infectious disease, shock, burn, endotoxinemia, organ inflammation, surgery, diabetes, collagen diseases, radiotherapy and chemotherapy is provided by the present invention.

DETAILED DESCRIPTION

Figure 1:
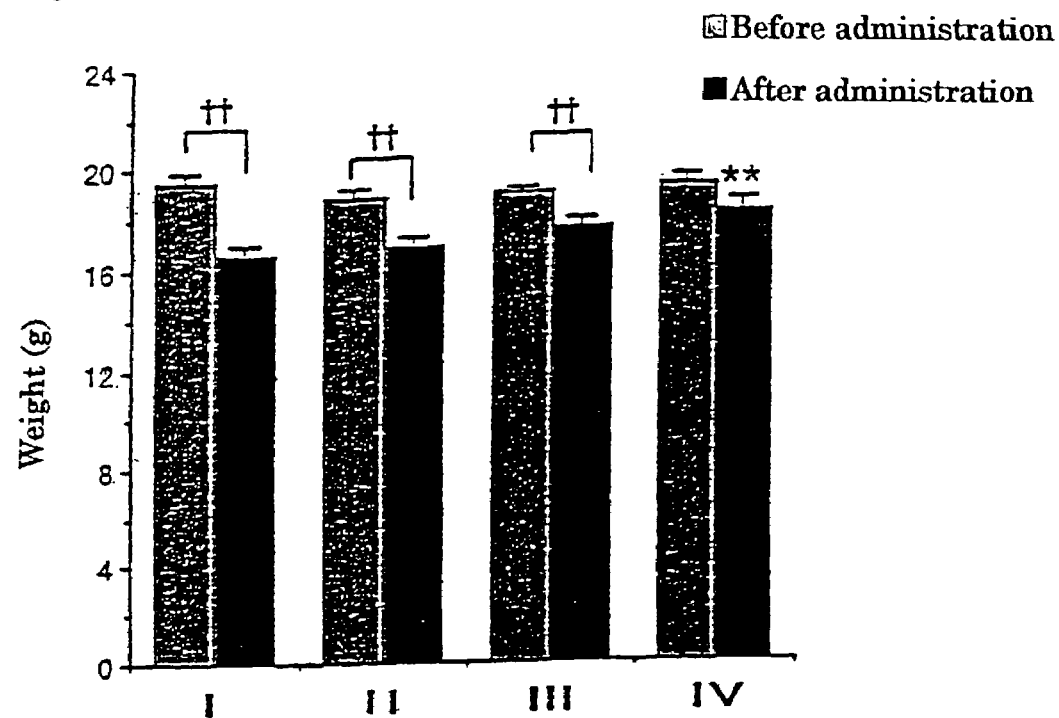
FIG. 1 shows an improving effect of TCF-II on weight loss in mice with transplanted KYN-2 cell as described in Example 1. (++) in the figure means significant difference ($p<0.01$) between before and after administration and (**) means significant difference ($p<0.01$) from Group I (the Control Group) after administration.

TCF-II which is an effective ingredient of the present invention is a known protein derived from human fibroblasts having the following characteristics:

1) Molecular weight (by SDS electrophoresis)
   under non-reducing conditions: $78,000\pm2,000$ or $74,000\pm2,000$
   under reducing conditions: $52,000\pm2,000$ (common band A)
   $30,000\pm2,000$ (band B)
   $26,000\pm2,000$ (band C)
2) Isoelectric point: 7.4–8.6

Isolation of TCF-II

The above TCF-II can be obtained by adsorbing culture medium of human fibroblast on an ion exchange column then purifying the elute by affinity chromatography (WO 90/10651) or by genetic engineering manipulation (WO 92/01053). TCF-II which is an effective ingredient of the present invention can be derived from fibroblasts or produced by genetic engineering manipulation using microbial organism or other cell as based on the genetic sequence described in WO 90/10651. Further, TCF-II obtained by genetic engineering manipulation described in WO 92/01053 can be also used. TCF-II with different carbohydrate chain or without carbohydrate chain due to difference of host cell or microbial organism can be also used. However, TCF-II with carbohydrate chain can be preferably used. TCF-II obtained by these methods can be concentrated and purified by usual isolation and purification methods, for example, precipitation with organic solvent, salting out, gel permeation, affinity chromatography using monoclonal antibody, electrophoresis. Purification by affinity chromatography can be carried out using the monoclonal antibody described in a Japanese unexamined laid open patent application No.97 (1993). The purified TCF-II can be lyophilized or kept frozen.

Substances having the same activity as TCF-II can be used as the agent of the present invention. For example, hepatocyte growth factor (HGF; Japanese unexamined laid-open patent application No.22526 (1988)) which is formed by insertion of 5 amino acids into TCF-II protein or purified Scatter Factor (SF;Gherardi and Stocker, Nature, 346, 228 (1990)) may be used as the agent of the invention.

The agent of the present invention for preventing and/or treating cachexia can be administered intravenously, intramuscularly or subcutaneously. These pharmaceutical preparations can be prepared according to a known pharmaceutical preparation method and, if necessary, pH conditioner, buffer and/or stabilizer can be added thereto. Dosage of the present agent may vary depending on the severness of symptom, health conditions, age, body weight of a patient. Though the dose will not be restricted, a pharmaceutical preparation comprising 0.6 mg–600 mg-TCF-II/day, preferably 6 mg–60 mg-TCF-II/day, for one adult person can be administered in a single dose or in multiple doses.

The present invention will be described below in detail by the following examples. However, these are only examples and the present invention will not limited therewith.

Purification of TCF-II

According to a method described in WO 90/10651 and a method of Higashio et al (Higashio, K. et. al, B.B.R.C., vol. 170, pp 397–404(1990)), fibroblast cells were cultured and purified TCF-II was obtained. That is, $3 \times 10^6$ human fibroblast IMR-90 (ATCC CCL-186) cells were placed in a roller bottle containing 100 ml of DMEM medium including 5% calf fetal serum and cultured by rotating it at the rate of 0.5–2 rpm for 7 days. When the total number of cell reached $1 \times 10^7$, cells were detached from the wall by trypsin digestion and collected at the bottom of bottle. 100 g of ceramic with the size of 5–9 mesh (Toshiba Ceramic) was added to the roller bottle. Cultured was continued for 24 hours. After then, 500 ml of the above culture medium was added and the culture was continued. The total volume of culture medium was recovered every 7–10 days and fresh medium was supplemented. Production proceeded for 2 months under these conditions, after which 4 liters of culture medium was recovered per roller bottle. Specific activity of TCF-II in culture medium obtained as above was 32 μg/ml. Culture medium (750 L) was concentrated by ultrafiltration using membrane filter (MW 6,000 cut; Millipore, Bedford, Mass.) and purified by 4-steps chromatography, that is, CM-Sephadex C-50 (Pharmacia, Peapack, N.J.), Con-A Sepharose (Pharmacia), Mono S column (Pharmacia), Heparin-Sepharose (Pharmacia) to yield purified TCF-II. This TCF-II had the same molecular weight and isoelectric point as described before.

Production of Recombinant TCF-II

According to the method described in WO 92/01053, cells transformed with TCF-II gene were cultured and purified TCF-II was obtained. That is, transformed Namalwa cells were cultured and 20 L of culture medium was obtained. This culture medium was treated by CM-sphadex C-50 chromatography, Con-A Sepharose CL-6B chromatography and finally HPLC equipped with a Mono S column to yield about 11 mg of recombinant TCF-II.

Manufacturing of Pharmaceutical Preparation of TCF-II

An example of manufacturing injections of TCF-II obtained as described above.

| (1) TCF-II | 20 μg |
|---|---|
| human serum albumin | 100 mg |

The above composition was dissolved in citric acid buffer solution with pH 6.03 so that the total volume should be 20 ml. Then it was divided into vials containing 2 ml each after sterilization and sealed after lyophilization.

| (2) TCF-II | 40 μg |
|---|---|
| Tween 80 | 1 mg |
| human serum albumin | 100 mg |

The above composition was dissolved in physiological saline solution for injections so that the total volume would be 20 ml. Then it was divided into vials containing 2 ml each after sterilization and sealed after lyophilization.

| (3) TCF-II | 20 μg |
|---|---|
| Tween 80 | 2 mg |
| Sorbitol | 4 g |

The above composition was dissolved in citric acid buffer solution with pH 6.03 so that the total volume would be 20 ml. Then it was divided into vials containing 2 ml each after sterilization and sealed after lyophilization.

| (4) TCF-II | 40 μg |
|---|---|
| Tween 80 | 1 mg |
| Glycine | 2 g |

The above composition was dissolved in physiological saline solution for injections so that the total volume would be 20 ml. Then it was divided into vials containing 2 ml each after sterilization and sealed after lyophilization.

| (5) TCF-II | 40 g |
|---|---|
| Tween 80 | 1 mg |
| Sorbitol | 2 g |
| Glycine | 1 g |

The above composition was dissolved in physiological saline solution for injections so that the total volume would be 20 ml. Then it was divided into vials containing 2 ml each after sterilization and sealed after lyophilization.

| (6) TCF-II | 20 μg |
|---|---|
| Sorbitol | 4 g |
| human serum albumin | 50 mg |

The above composition was dissolved in citric acid buffer solution with pH 6.03 so that the total volume would be 20 ml. Then it was divided into vials containing 2 ml each after sterilization and sealed after lyophilization.

| (7) | TCF-II | 40 μg |
| | Glycine | 2 g |
| | human serum albumin | 50 mg |

The above composition was dissolved in physiological saline solution for injections so that the total volume would be 20 ml. Then it was divided into vials containing 2 ml each after sterilization and sealed after lyophilization.

| (8) | TCF-II | 40 μg |
| | human serum albumin | 50 mg |

The above composition was dissolved in citric acid buffer solution with pH 6.03 so that the total volume would be 20 ml. Then it was divided into vials containing 2 ml each after sterilization and sealed after lyophilization.

EXAMPLE 1

Effect of TCF-II Administration Against Cachexia in Mice with Transplanted Human Hepatocellular Carcinoma A transplanted human hepatocellular carcinoma, KYN-2 cell line or KYN-3 cell line which show proliferation or cell dispersion in preliminary experiment in vitro was used. Static culture of either cell line was carried out using Dulbecco's MEM medium (Nissui-seiyaku) containing 100 U/ml penicillin, 100 μg/ml streptomycin (Gibco Life Technologies, Rockville, Md.), 12 m mol/L sodium bicarbonate, 20% heat-inactivated calf serum (Whittaker Bioproducts Walkersfield, Md.) at 37° C., 5% $CO_2$ and 100% humidity. After trypsin-EDTA was added to both of the cultured cell lines, cells were separated, washed twice with phosphate buffer solution (PBS) and resuspended at a concentration of $2.0 \times 10^7$ cell/ml.

After shaving hair on skin of transplantation site in 4–5 weeks old female SCID, disinfecting the site with 70% ethanol and ether anesthesia, tumor cell prepared beforehand was transplanted into the mice using 23 G syringe needle. KYN-2 cell line ($1.0 \times 10^7$) was transplanted subcutaneously into animal's back and KYN-3 ($1.0 \times 10^7$) was transplanted intraperitoneally. On 3 weeks after subcutaneous transplantation of KYN-2 cell line when the diameter of tumor became 5 mm and on 5 weeks after intraperitoneal transplantation of KYN-3 cell line, these mice with transplanted tumor cells were divided into 4 groups, respectively. Mice in I, II, III and IV groups were administered with vehicle (i.e., no TCF-II), 0.3 mg-TCF-II/kg/day, 3.0 mg-TCF-II/kg/day and 30 mg-TCF-II/mg/kg, respectively. Twice a day for 2 weeks, TCF-II was intraperitoneally administered in mice with transplanted KYN-2 cell line and was subcutaneously administered in mice with transplanted KYN-3 cell line.

Body weight was determined before and after administration in mice with subcutaneous transplanted KYN-2 cell line. Hematocrit was measured before and after administration of TCF-II by taking blood sample with hematocrit heparinized capillary (Termo) from ocular fundus artery under ether anesthesia in mice with KYN-3 and centrifuging it in a usual method. Then, TNF level in ascite was measured using Factor-Test-XTM Mouse TNF ELISA kit (Genzyme Cambridge, Mass.) after TCF-II administration and autopsy under ether anesthesia. Easy Reader EAR 400 (SLT Laboinstruments) was used in absorptiometry.

Body weight change in vehicle-administered group and TCF-II administered groups are shown in FIG. 1. In the vehicle-administered group (Group I), body weight was significantly lost (about 20% loss) during 2 weeks. On the other hand, body weight loss was suppressed in a dose dependant manner in TCF-II administered groups. Especially in Group IV, there was no significant difference before and after administration and, furthermore, body weight in Group IV was clearly higher than that in Group I after administration.

Figure 2:
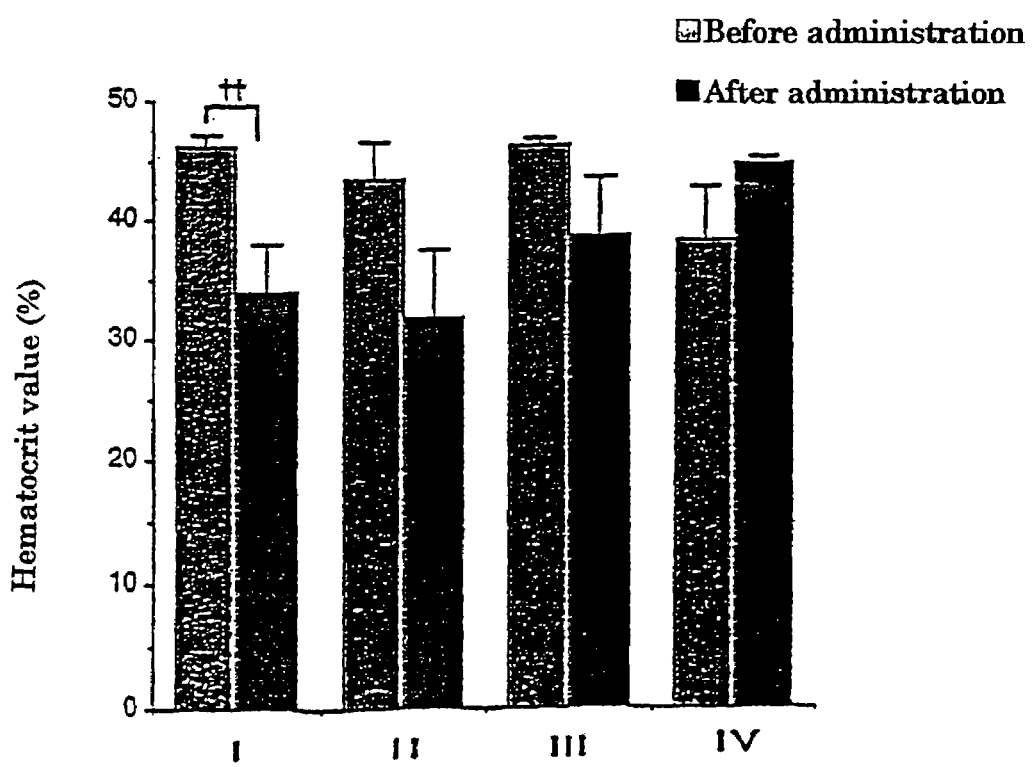
FIG. 2 shows an improving effect of TCF-II on lowered hematocrit value in mice with transplanted KYN-3 cell as described in Example 1. (++) in the figure means significant difference ($p<0.01$) between before and after administration.
Figure 3:
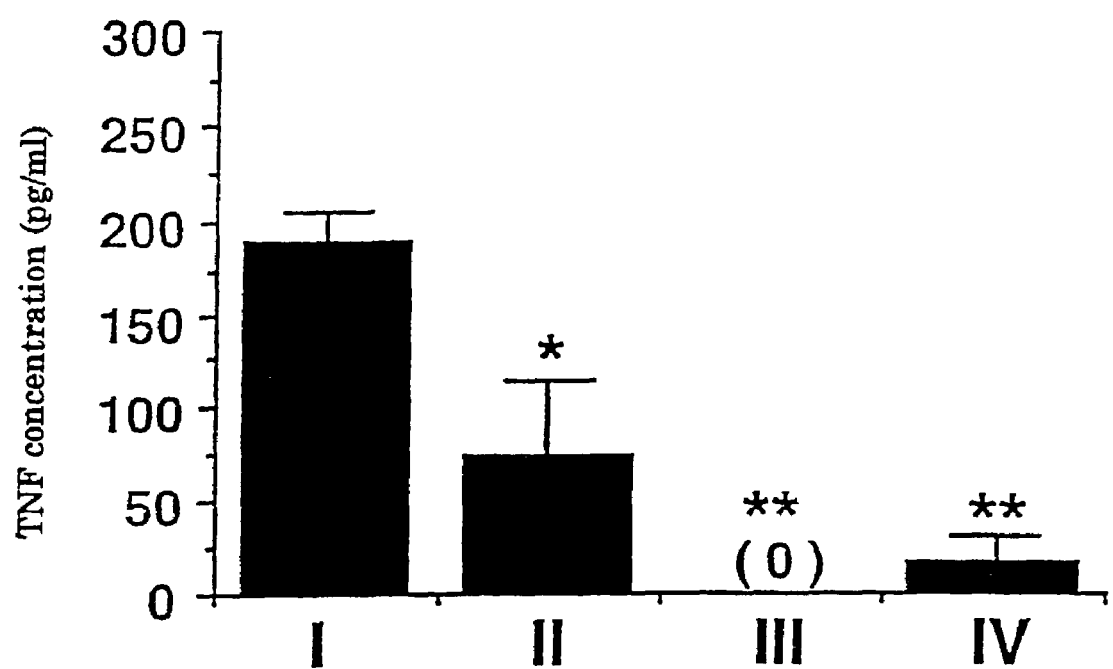
FIG. 3 shows a suppressing effect on elevated TNF in ascites of mice with transplanted KYN-3 cell as described in Example 1. (*) in the figure means significant difference ($p<0.05$) from Group I (the Control Group) and (**) means significant difference ($p<0.01$) from Group I (the Control Group).

Hematocrit change in vehicle-administered group and TCF-II administered groups was shown in FIG. 2. By administration of TCF-II, the hematocrit level in mice with cancer was improved and the progress of anemia accompanying with tumor proliferation was suppressed. Further, the suppressive effect of TCF-II on TNF elevation was shown in FIG. 3. TNF, which was a cause of cachexia in animals with cancer, was significantly lowered in a dose dependant manner by TCF II administration and significant suppression was observed even in Group II which was administered with the minimum dose of 0.3 mg/kg/day. The results shown in FIGS. 1–3 demonstrate TCF-II administration significantly improved cachexia that is body weight loss caused by cancer proliferation, progress of anemia and elevation of TNF.

From what was described as above, a useful agent for preventing and treating cachexia caused by one of the factors selected from the group consisting of cancer, acquired immunodeficient syndrome (AIDS), cardiac diseases, infectious disease, shock, burn, endotoxinemia, organ inflammation, surgery, diabetes, collagen diseases, radiotherapy and chemotherapy is provided by the present invention.

The invention claimed is:

1. A method for reducing the TNF-α level in a patient having a cancer comprising the steps of:
   administering Tumor Cytotoxic Factor II to the cancer patient in a dosage between about 0.3 mg/kg body weight/day and about 30 mg/kg body weight/day, and determining the level of TNF-α in the patient after the administration of Tumor Cytotoxic Factor II.

2. The method of claim 1, wherein Tumor Cytotoxic Factor II is administered by injection.

3. The method of claim 1, wherein Tumor Cytotoxic Factor II is dispersed in a composition comprising saline or citric acid.

4. The method of claim 1, wherein the patient is a human patient.

* * * * *